US010718831B2

(12) United States Patent
Halkola et al.

(10) Patent No.: US 10,718,831 B2
(45) Date of Patent: Jul. 21, 2020

(54) MAGNETIC RESONANCE IMAGING RECEIVE COIL WITH REDUCED RADIATION ATTENUATION

(71) Applicant: KONINKLIJKE PHILIPS N.V., Eindhoven (NL)

(72) Inventors: Annemaria Johanna Halkola, Eindhoven (NL); Mika Petri Ylihautala, Eindhoven (NL); Wycliffe Adell Raduma, Eindhoven (NL); Tero Jouko Valtter Virta, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 451 days.

(21) Appl. No.: 15/505,259

(22) PCT Filed: Aug. 7, 2015

(86) PCT No.: PCT/EP2015/068258
§ 371 (c)(1),
(2) Date: Feb. 21, 2017

(87) PCT Pub. No.: WO2016/034364
PCT Pub. Date: Mar. 10, 2016

(65) Prior Publication Data
US 2017/0252578 A1    Sep. 7, 2017

(30) Foreign Application Priority Data
Sep. 1, 2014   (EP) .................................... 14183088

(51) Int. Cl.
*A61B 5/055*   (2006.01)
*A61N 5/10*    (2006.01)
(Continued)

(52) U.S. Cl.
CPC .............. *G01R 33/34* (2013.01); *A61B 5/055* (2013.01); *A61N 5/1049* (2013.01);
(Continued)

(58) Field of Classification Search
CPC .............. G01R 33/4812; G01R 33/481; G01R 33/34007; G01R 33/34084;
(Continued)

(56) References Cited

U.S. PATENT DOCUMENTS 6,060,882 A * 5/2000 Doty ................ G01R 33/34046
324/318
7,526,330 B1 * 4/2009 Randell ................... A61B 5/055
324/309
(Continued)

OTHER PUBLICATIONS

Christin Y.Sander et al: "A 31-channel MR brain array coil compatible with positron emission tomography", Magnetic Resonance in Medicine., vol. 73, No. 6, Jul. 7, 2014 (Jul. 7, 2014), pp. 2363-2375.*
(Continued)

*Primary Examiner* — Angela M Hoffa
*Assistant Examiner* — Victoria Fang
(74) *Attorney, Agent, or Firm* — Sherry Austin

(57) ABSTRACT

A magnetic resonance antenna includes a surface coil and a receive coil. The magnetic resonance antenna includes one or more antenna elements. The magnetic resonance antenna further includes a preamplifier for the antenna element and a coil former for supporting the antenna element. The coil former is formed from a porous material. The antenna is divided into an irradiation zone and at least one reduced radiation zone. The preamplifier for each of multiple antenna elements is located within the at least one reduced radiation zone. The multiple antenna elements are located at least partially within the irradiation zone. The coil former has a perimeter. The irradiation zone extends continuously from a
(Continued)

first edge of the perimeter to a second edge of the perimeter. The first edge and the second edge are opposing edges.

26 Claims, 8 Drawing Sheets

(51) Int. Cl.
G01R 33/34 (2006.01)
G01R 33/341 (2006.01)
G01R 33/3415 (2006.01)
G01R 33/48 (2006.01)

(52) U.S. Cl.
CPC ..... *G01R 33/341* (2013.01); *G01R 33/34007* (2013.01); *G01R 33/3415* (2013.01); *G01R 33/4812* (2013.01); *A61B 2562/17* (2017.08); *A61N 2005/1055* (2013.01)

(58) Field of Classification Search
CPC ............ G01R 33/34092; G01R 33/341; G01R 33/3415; G01R 33/3621; G01R 33/3628–3664; A61N 2005/1055; A61N 5/1039; A61N 2005/1094–1096; A61N 5/1049; A61B 2562/17; A61B 2562/18; A61B 2562/182; G01N 30/6082; Y01S 606/912
USPC ........................................................ 600/410
See application file for complete search history.

(56) References Cited

U.S. PATENT DOCUMENTS

| 2006/0273795 | A1* | 12/2006 | Rieke | A61B 5/055 324/318 |
| 2008/0100297 | A1* | 5/2008 | Ishii | G01R 33/3415 324/322 |
| 2009/0177077 | A1* | 7/2009 | Piferi | G01R 33/285 600/414 |
| 2010/0010337 | A1* | 1/2010 | Hagen | A61B 5/0555 600/411 |
| 2010/0066373 | A1* | 3/2010 | Arnold | G01R 33/3415 324/318 |
| 2011/0012593 | A1* | 1/2011 | Shvartsman | G01R 33/3806 324/307 |
| 2011/0074420 | A1* | 3/2011 | Ladebeck | G01R 33/34046 324/318 |
| 2011/0267059 | A1* | 11/2011 | Shvartsberg | G01R 33/34007 324/318 |
| 2012/0286786 | A1* | 11/2012 | Schellekens | G01R 33/3415 324/322 |
| 2013/0027040 | A1* | 1/2013 | Alagappan | G01R 33/34007 324/322 |
| 2013/0225975 | A1* | 8/2013 | Harvey | A61B 5/0037 600/411 |
| 2015/0224341 | A1 | 8/2015 | Vahala et al. | |

OTHER PUBLICATIONS

Champagne et al "A Novel Radiolucent Phased Array Design Suitable for MR Guided Radiation Therapy" Proc. Intl. Soc. Mag. Reson. Med 19 (2011).
Viola Rieke et al: "X-ray compatible radio frequency coil for magnetic resonance imaging", Magnetic Resonance in Medicine, John Wiley & Sons, Inc, US,vol. 53, No. 6, Jun. 1, 2005 (Jun. 1, 2005), pp. 1409-1414.

* cited by examiner

MAGNETIC RESONANCE IMAGING RECEIVE COIL WITH REDUCED RADIATION ATTENUATION

CROSS REFERENCE TO RELATED APPLICATIONS

This application is a U.S. national phase application of International Application No. PCT/EP2015/068258, filed on Aug. 7, 2015, which claims the benefit of EP Application Serial No. 14183088.5 filed on Sep. 1, 2014 and is incorporated herein by reference.

TECHNICAL FIELD OF THE INVENTION

The invention relates to radiotherapy, in particular to radiotherapy combined with magnetic resonance imaging.

BACKGROUND OF THE INVENTION

In routine practice of Radiotherapy (RT), the subject is positioned relative to the stationary center of the rotating arc carrying the RT source. Positioning implies both height and lateral adjustment of the subject table. This positioning is required to optimize the dose in the lesion beyond variation that can be obtained by applying RI rays from different angles.

Integration of MR and Linear Accelerators (LINAC) opens new horizons in Radiotherapy by improved lesion targeting, especially for moving organs. In a practical implementation proposal, the LINAC rotates around the subject to hit the gross target volume (GTV) and clinical target volume (M) from multiple angles while minimizing the radiation exposure for surrounding tissues.

The combination of magnetic resonance apparatuses and LINAC radiotherapy sources is known. Typically a LINAC source is placed on a rotating gantry about the magnet and designing the magnet such that the LINAC rotates in a zero-field region of the magnet. Another particular feature of the concept is the use of a split gradient coil which prevents attenuation of the LINAC beam.

In Champagne et. al. "A Novel Radiolucent Phased Array Design Suitable for MR Guided Radiation Therapy," Proc. Intl. Soc. Mag, Resort. Med 19 (2011) an X-ray transparent phased array coil for magnetic resonance imaging is described. The coil was constructed so that a combination of thicknesses of copper and the solid FR4 substrate such that it will be transparent during x-ray imaging and radiation therapy.

SUMMARY OF THE INVENTION

The invention provides for a magnetic resonance antenna and a medical instrument in the independent claims embodiments are given in the dependent claims.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and. Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wireline, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as JAVA®, SMALLTALK, C++, or the like and conventional procedural programming languages, such as the "C" programming language or similar programming languages and compiled into machine executable instructions. In some instances the computer executable code may be in the form of a higher level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, BLUETOOTH® connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins by the antenna of a Magnetic resonance apparatus during a magnetic resonance imaging scan. Magnetic resonance data is an example of medical image data. A Magnetic Resonance Imaging (MRI) image is defined herein as being the reconstructed two or three dimensional visualization of anatomic data contained within the magnetic resonance imaging data. This visualization can be performed using a computer. A portion of magnetic resonance data may also refer to a "shot." Navigator data is an example of magnetic resonance data, and is typically representative of a subject's location or state of motion.

In one aspect the invention provides for a magnetic resonance antenna. The magnetic resonance antenna is a surface coil. The magnetic resonance antenna is a receive coil. The magnetic resonance antenna comprises one or multiple antenna elements. The one or multiple antenna elements are conductive and are thin as to limit only blocking X-ray radiation. The one or multiple antenna elements could for example comprise copper, silver, aluminum. The one or multiple antenna elements could for example be formed from copper strips. The magnetic resonance antenna further comprises a pre-amplifier for the multiple antenna elements or a combination of antenna elements. The magnetic resonance antenna further comprises a coil former for supporting one or more of the antenna elements. The coil former is formed from a porous material. The coil former is divided into an irradiation zone and at least one reduced radiation zone. The pre-amplifier for each of the one or multiple antenna elements is located within the at least one reduced radiation zone. The one or multiple antenna elements are located at least partially within the irradiation zone. The coil former has a perimeter that forms edges. The magnetic resonance antenna is a surface coil. So although the surface coil may not be flat it predominantly has a surface which is bounded by edges. The edges extend about the perimeter of the surface coil. The irradiation zone extends continuously from a first edge of the perimeter to a second edge of the perimeter. The first edge and the second edge are opposing or opposite edges. This example or embodiment may be useful because the use of the porous material may reduce the absorption of X-ray radiation in comparison to a solid material. 'X-ray' radiation as used here encompasses energetic photons ranging in energy between 100 eV to 10 MeV. In the specification and claims X-ray may be substituted with Gamma radiation. Gamma radiation as used here encompasses 500 keV to 10 MeV. The use of a porous material may also enables a structurally stronger antenna in comparison to a solid material.

In some magnetic resonance antennas which are used with X-ray systems the thickness of the material used for the coil former is changed so that it balances or makes the absorption of radiation by the magnetic resonance antenna uniform. However for irradiating a magnetic resonance antenna with the X-ray radiation this is not desirable. It is more desirable to reduce the amount of radiation absorbed by the magnetic resonance antenna as much as possible.

The use of a porous material in comparison to FR4 or other materials is that the porous material may be easier to form into different shapes. Also the use of a porous material may reduce Compton scattering. The use of a porous material may also provide for a magnetic resonance antenna has a larger bulk and/or is more mechanically stable in comparison to an antenna made of other materials.

In another embodiment the coil former is laminated to the one or multiple antenna elements.

In another embodiment the one or multiple antenna elements are formed on a flexible printed circuit board. The flexible printed circuit board may be glued or laminated to the coil former.

In another embodiment the coil former is rigid.

In another embodiment the porous material is any one of the following: A foam, expanded polypropylene, Polyurethane foam, Polyimide foam, Polyether ether ketone (PEEK) foam, a corrugated structure, corrugated cardboard, a honeycomb structure, and/or has an attenuation of less than 2% for X-ray radiation between 1.8 mega electron volts and 8 MeV. In another embodiment the porous material has an attenuation of less than 1% for X-ray radiation between 1.8 MeV and 8 MeV.

In another embodiment the coil former is rigid. The coil former is formed from a solid plastic between 0.2 and 0.8 millimeters thick.

As alternative, the coil former may also be formed from a polycarbonate layer between 0.2 and 0.8 millimeters thick.

In another embodiment a cross-section of the coil former from the first edge to the second edge is predominantly concave when observed from a direction from the coil former to the multiple antenna elements. The concave shape is when the observer is looking in the direction of the magnetic resonance antenna and the coil former is closer to the observer than the multiple antenna elements.

Alternatively the cross-section of the coil former from the first edge to the second edge is predominantly convex when observed from a direction from the surface as will be defined later in the text below.

In another embodiment a cross-section of the coil former from the first edge to the second edge is at least partially curved or is curved to form a convex surface.

In another embodiment the magnetic resonance antenna is rectangular or predominantly square in shape.

In another embodiment the cross-section is any one of the following: a semi circle, comprises straight segments and rounded segments, generally flat with rounded portions near the first edge and the second edge and a series of connected straight segments.

In another embodiment the coil former comprises one or more mounting fixtures for attaching a magnetic resonance antenna to a subject support. This embodiment may be beneficial because the magnetic resonance antenna may be affixed to the subject support with a known geometrical relationship. In this case it may be possible to take into account the absorption of radiation by the magnetic resonance antenna during a X-ray radiation therapy.

In another embodiment the coil former is flexible. For example the coil former may be made from a flexible plastic. In other examples the coil former may be a fabric or a textile. In other examples the coil former may be made from a non-woven fiber or non-woven fabric. For instance a paper, natural fiber, or other such structure may be used.

In another embodiment the one or multiple antenna elements (e.g. a copper strip) is formed on a flexible printed circuit board. The flexible printed circuit board is attached to the coil former. This may be alternatively worded in that the one or multiple antenna elements comprise a flexible printed circuit board. The flexible printed circuit board may be laminated or glued to the coil former. This embodiment may be beneficial because the flexible printed circuit board may be an efficient way of manufacturing the one or multiple antenna elements. Particularly when the one or multiple antenna elements with the printed circuit board are attached to the coil former this may provide for a magnetic resonance antenna which is mechanically stable.

In another embodiment the at least one reduced radiation zone is two or more reduced radiation zones. The two or more reduced radiation zones comprises PIN diodes for controlling detuning of the one or multiple antenna elements. The irradiation zone comprises flat conductors (e.g. copper conductors) for carrying electrical signals between the two or more reduced radiation zones for controlling the switching of the PIN diodes. In some examples the flat conductors are also formed on the printed circuit board. In other examples the flat conductors are much narrower than the strips used to form the one or multiple antenna elements. This may cause the impedance of the copper conductors to be much higher at radio frequency which the magnetic resonance system may be operating at. This may allow DC signals to be carried by the flat conductors but the high impedance of the flat conductors may help reduce them picking up and carrying a RF signal from the magnetic resonance imaging system. For instance the width of the flat conductors could be made approximately one third, one fourth, one fifth or one tenth of the width of the strips used to form the one or multiple antenna elements. At radio frequencies the surface area of the conductor is important if the surface area is reduced then the impedance increases.

In another embodiment, the conductors are copper conductors and the copper conductors have a width of approximately 3 mm, or 2.5 mm to 3.5 mm wide.

In another embodiment the copper strips have a width of approximately 1 mm, or 0.5 mm to 1.4 mm.

In another embodiment the magnetic resonance antenna has a first surface and a second surface. The coil former is between the first surface and the one or multiple antenna elements. The one or multiple antenna elements are between the second surface and the coil former. The magnetic resonance antenna further comprises a biocompatible layer that forms the first surface. The magnetic resonance antenna further comprises an outer layer that forms the second surface. This may be beneficial because the biocompatible layer and the outer layer may add extra mechanical stability to the magnetic resonance antenna. They may also be used to protect the coil former and the one or multiple antenna elements. For instance the porous material may be sealed so that the biocompatible layer does not allow it to absorb liquids.

The outer layer may also help to protect a subject from any RF voltage induced on the one or multiple antenna elements.

In another embodiment the porous material is the biocompatible layer or has a biocompatible surface exposed.

In another embodiment the biocompatible layer is any one of the following: Ethylene-vinyl acetate, PVC foam, polyurethane (PU) foam, PEEK foam, and Polyvinyl chloride (PVC) foam.

In another embodiment the outer layer is any one of the following: Ethylene-vinyl acetate, PVC foam, and polyurethane foam, PEEK foam, and PVC foam.

In another embodiment, the product of density and thickness of the core foam is less than 1.2 kg/m^2, less than 0.5 kg/m^2 for the surface foam, or less than 2.5 kg/m^2 for all materials in the irradiation zone. This is equivalent to limiting the attenuation to less than less than 0.8%.

In another embodiment the biocompatible layer is laminated to the coil former.

In another embodiment the outer layer is laminated to the one or multiple antenna elements. If the one or multiple antenna elements comprises a flexible printed circuit board then the outer layer is laminated to the flexible printed circuit board. The lamination of the biocompatible layer to the coil former and/or the lamination of the outer layer to the one or multiple antenna elements may be beneficial because it provides mechanical stability to the magnetic resonance antenna while only increasing the absorption of X-ray radiation by the magnetic resonance antenna only a small amount.

In another embodiment the thickness of the porous material is uniform. Using a uniform thickness of the porous material may be beneficial in that the absorption of radiation is minimized.

In another aspect the invention provides for a medical instrument comprising a LINAC with a X-ray source for directing X-ray radiation at a target zone. The LINAC is adapted for rotating the X-ray source about a rotational axis. The medical instrument further comprises a magnetic resonance imaging system for acquiring magnetic resonance data with a magnetic resonance antenna from an imaging zone. The magnetic resonance antenna is according to an embodiment. The target zone is within the imaging zone. The X-ray source is adapted for rotating at least partially about the magnet. This medical instrument may have the advantage that the resource delivers X-ray radiation more efficiently to the target zone using the magnetic resonance antenna.

In another embodiment the medical instrument further comprises a processor for controlling the medical instrument. The medical instrument further comprises a memory for storing machine executable instructions for execution by the processor. Execution of the machine executable instructions causes the processor to receive a treatment plan for irradiating the target zone. Execution of the machine executable instructions further causes the processor to acquire the magnetic resonance data using the magnetic resonance imaging system. Execution of the machine executable instructions further causes the processor to reconstruct a magnetic resonance image from the magnetic resonance data.

Execution of the instructions further cause the processor to register a location at the target zone in the magnetic resonance image. Execution of the machine executable instructions further causes the processor to generate control signals in accordance or using the location of the target zone and the treatment plan. Execution instructions further cause the processor to control the LINAC to irradiate the target zone using the control signals.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which.

DETAILED DESCRIPTION

Like numbered elements in these figures are either equivalent elements or perform the same function. Elements which have been discussed previously will not necessarily be discussed in later figures if the function is equivalent.

In some examples of a combined magnetic resonance (MR) imaging system and a LINAC, the receive coils or antenna of the MR LINAC system are placed as close as possible to the treated and imaged anatomy to maximize image quality and enable MR LINAC system to provide efficient MR guidance for the radiation beam. As a consequence, receive coils are located in the radiation beam path and this results that the coils attenuate and may cause non-idealities in the radiation therapy which may need to be taken into account in the delivery of the treatment. The receive coils are also exposed to relatively high radiation dose, that may affect the properties of the materials and electronics decreasing the overall lifetime of the coils.

A coil that minimally disturbs the radiation beam and the operation of which is minimally affected by the irradiation is crucial in the MR Linac application.

Examples may have an irradiation zone that enables radiation to pass through the coil minimally disturbing the dose delivery to the target or to other organs. The attenuation of the irradiation zone can be such that the attenuation can be neglected in the treatment planning. This streamlines user workflow and thus enables faster treatment planning and dose delivery.

The irradiation zone of the coil increases the reliability of the coil in the high dose environment. The sensitive electronics and materials are not located within the zone, which minimizes the amount of accumulated dose in the sensitive parts over the lifetime of the coil.

In some examples the irradiation zone within a receive coil can have one or more of the following elements:
- An area within the coil that is free of discrete electronic components
- An area that has minimized attenuation been made of low density materials, the structure construction can be rigid
- An area that has electrical conductors that minimally disturb the radiation beam
- A coil where the effect of radiation on the electronics is minimized by the placement and/or shielding.

Figure 1:
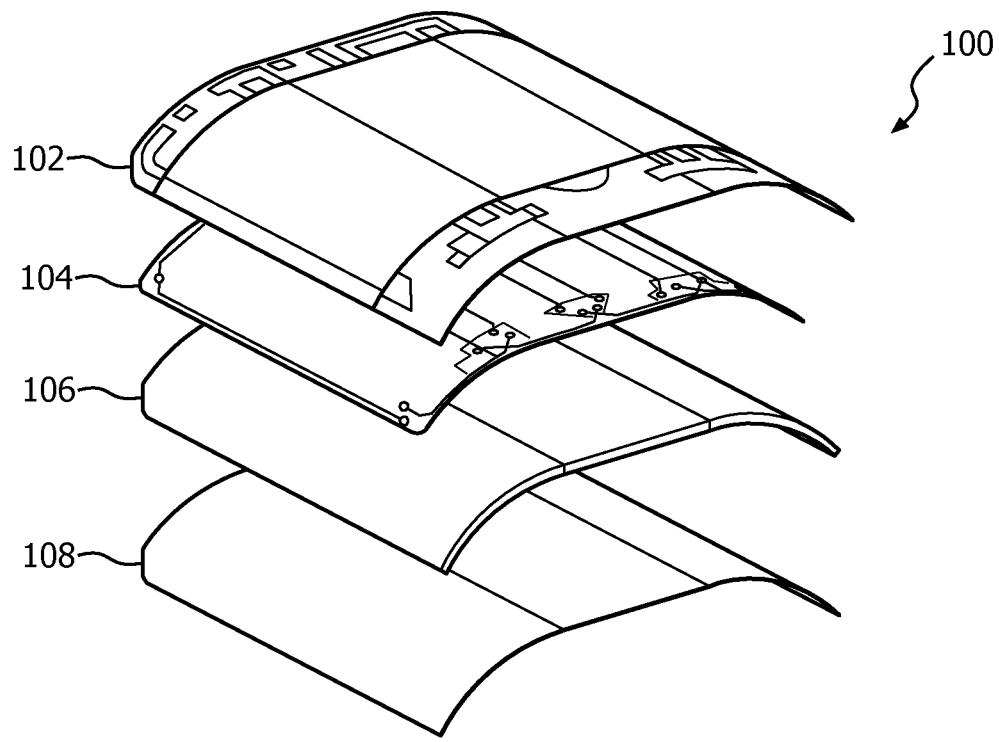
FIG. 1 shows an exploded view of an example of a magnetic resonance antenna.

FIG. 1 shows an example of a magnetic resonance antenna 100. In the antenna 100 is a composite made out of a variety of layers. In FIG. 1 these layers are shown in an expanded view. There is an outer layer 102 that is in contact with a flexible printed circuit board 104. The flexible printed circuit board 104 contains the one or multiple antenna elements. The flexible printed circuit board 104 is then connected to a coil former 106. The coil former 106 in this example is a rigid foam or porous material. The coil former 106 is then connected to a biocompatible layer 108 that may be in contact with a subject. These four layers may be glued or laminated together to form a rigid magnetic resonance antenna.

Figure 2:
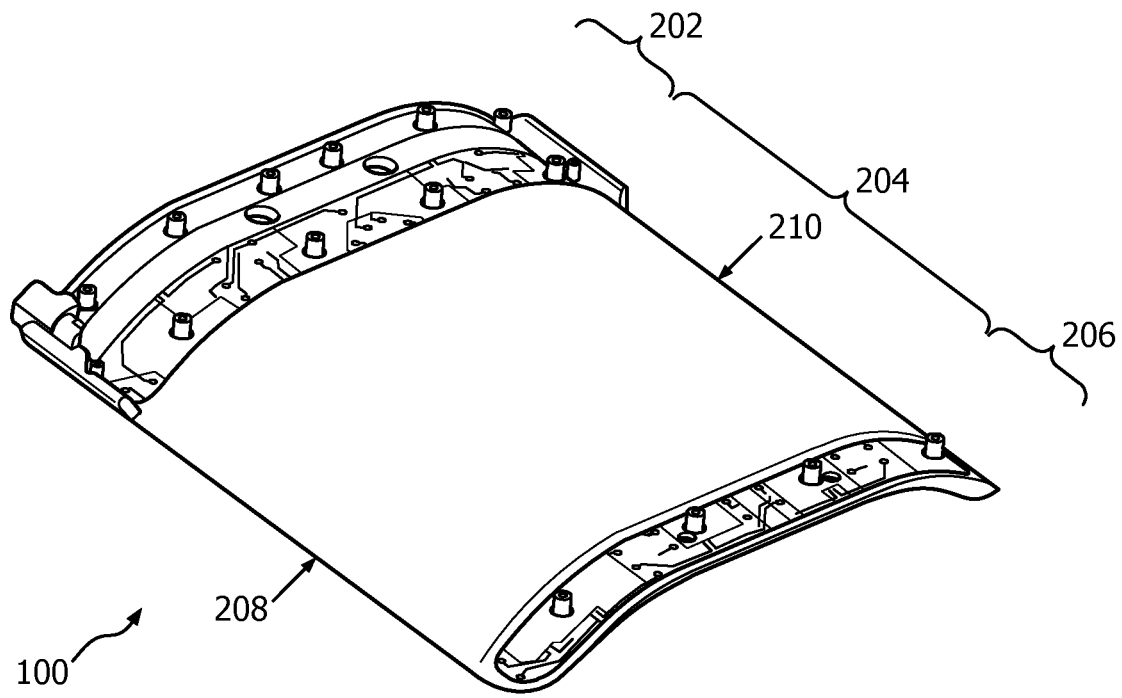
FIG. 2 shows the magnetic resonance antenna of FIG. 1 in assembled form.

FIG. 2 shows the antenna 100 after it has been laminated together. The coil 100 is a surface coil that is a bit curved. On one side there is a first reduced radiation zone 202. In the middle of the coil 100 there is an irradiation zone 204. And on the other end there is a second reduced radiation zone 206. In the irradiation zone 204 there are no electronic components electronic components have been moved to the first reduced radiation zone 202 and the second reduced radiation zone 206. There is a perimeter about this antenna 100. It can be seen there is a first edge 208 and a second edge 210 that are on opposite sides of the antenna 100. A cross-section or line can be drawn from the first edge 208 to the second edge 210 that stays within the irradiation zone 204. The antenna shown in FIGS. 1 and 2 may be used in a LINAC system. The possible area where the beam may travel is aligned with the irradiation zone 204 and the electronics in the first reduced radiation zone 202 and the second reduced radiation zone 206 are kept out of the X-ray beam path.

Figure 8:
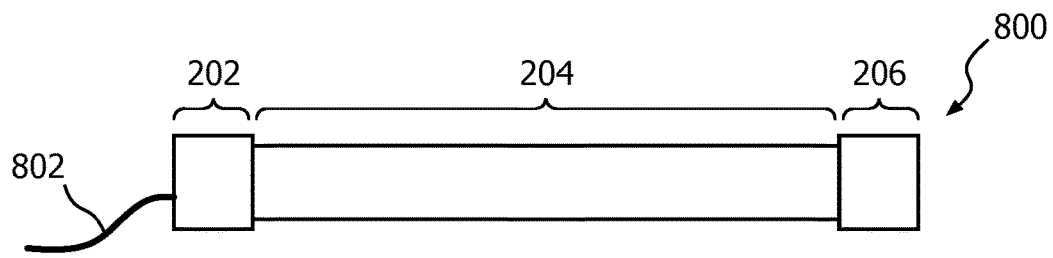
FIG. 8 shows a cross sectional view of a further example of a magnetic resonance antenna.
Figure 9:
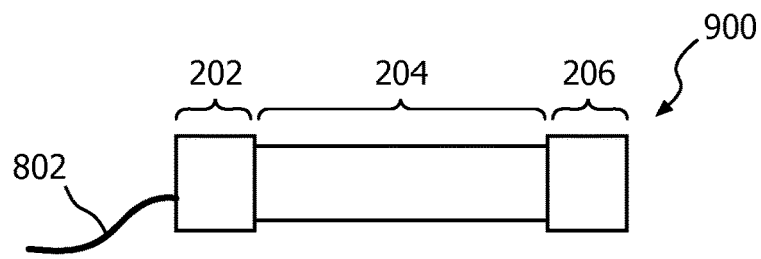
FIG. 9 shows a cross sectional view of a further example of a magnetic resonance antenna.
Figure 10:
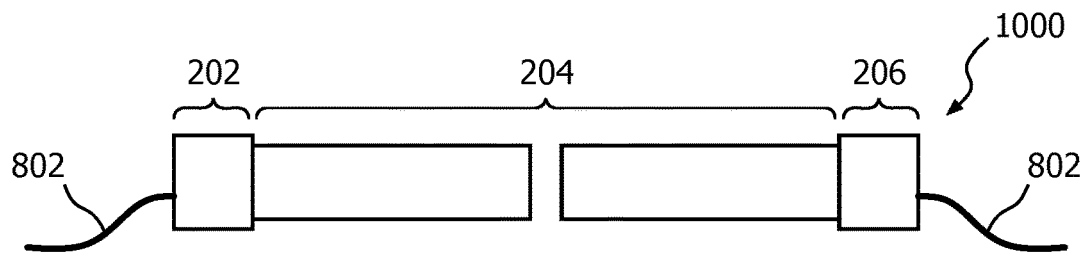
FIG. 10 shows a cross sectional view of a further example of a magnetic resonance antenna.

The irradiation zone of the structure is where the materials mentioned above create maximally homogenous area within the coil, i.e. may have no cutouts or other materials or components in it. This irradiation zone can be in the middle of the coil, or in one end of the coil. In case the irradiation zone is in one end of the coil, the coil can be used in combination with other similar coil. The irradiation zone placements within the coil are shown in FIGS. 8, 9, and 10. The irradiation zone placed on the beam path has a length of greater than the radiation beam itself.

The magnetic resonance receive coil may have the feature of a mechanical structure of low density materials or foam that may be rigid. The structure can be made of various alternative materials in a form sandwich that enhances the rigidity of the structure, as shown in FIG. 1.

The core of the structure is made of rigid, low density foam or material e.g. EPP (Expanded polypropylene). The material can be either machined or molded to its form. This part forms the basis for the structure in terms of rigidity. The density of the material is low, ~100 kg/m3.

The outer surface of the structure is made of low density soft foam or material e.g. EVA (Ethylene-vinyl acetate). This foam or material is providing the biocompatible surface for the structure. Due to its closed cell structure, it also prevents liquids to ingress the structure. The material density is ~50 kg/m3.

In between the foam or material layers, the coil winding printed circuit board (PCB) is assembled. The foam or low density materials mentioned above and the PCB in between are thereto molded together to form the final structure and shape of the product. A thin layer of glue is attached between each layer to keep the layers firmly attached.

Figure 3:
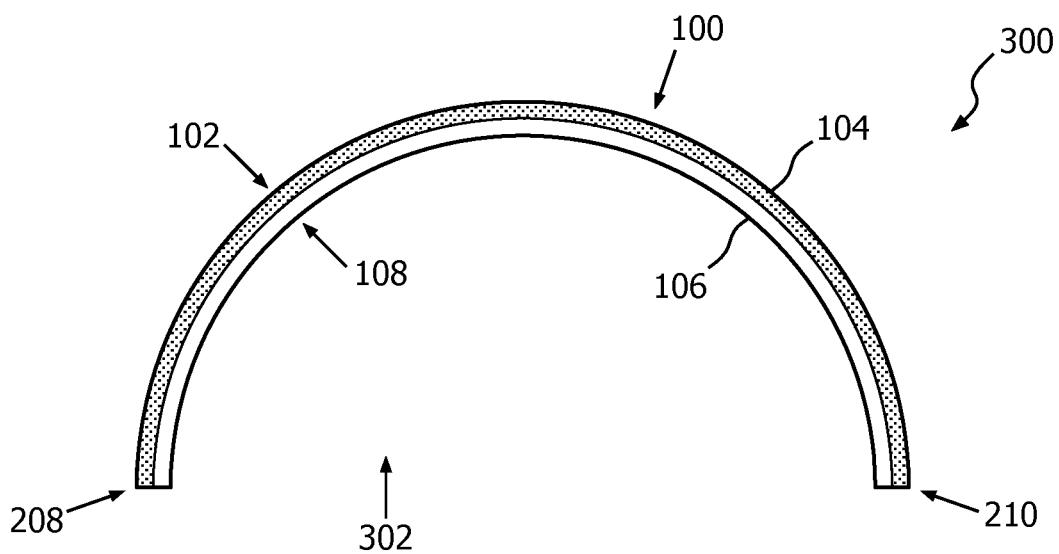
FIG. 3 shows a cross sectional view of a further example of a magnetic resonance antenna.
Figure 4:
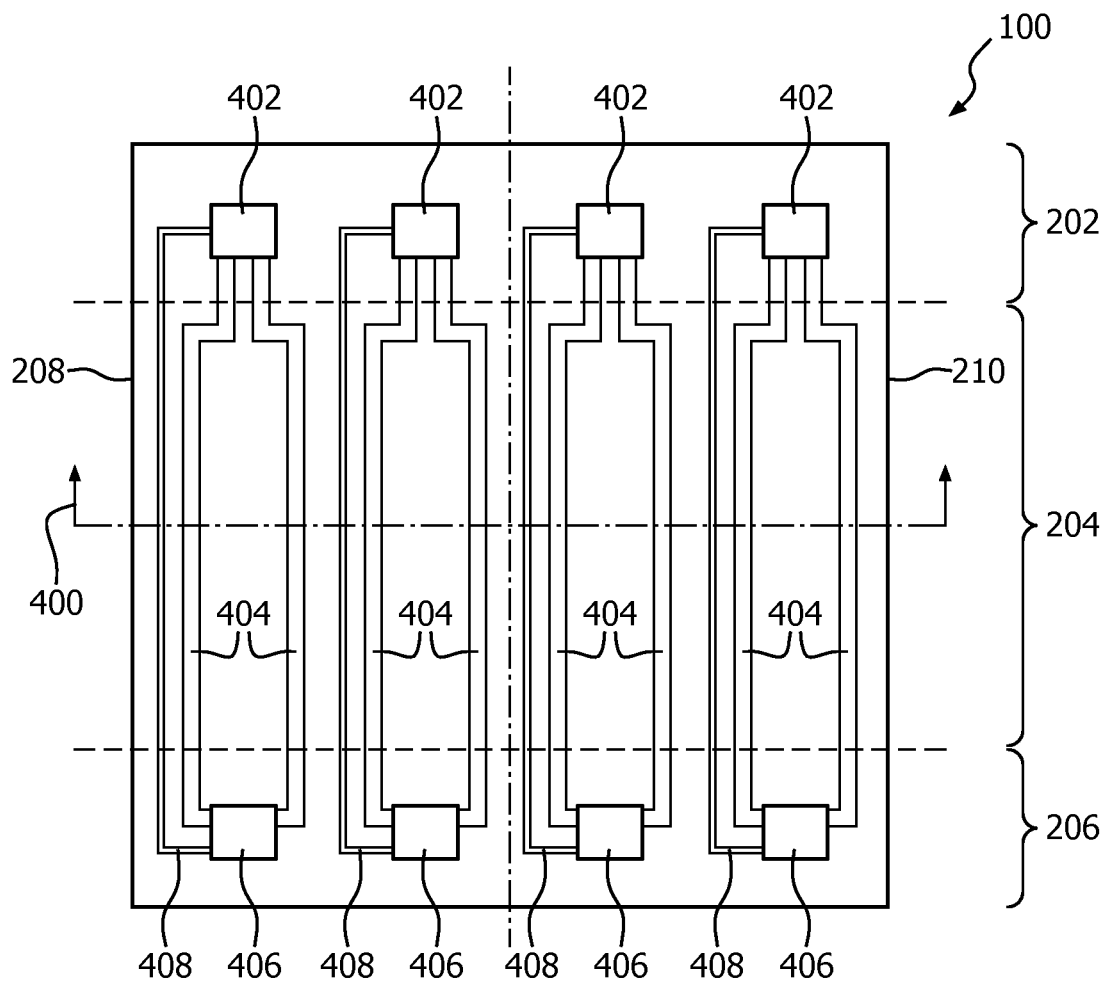
FIG. 4 shows a top view of a further example of a magnetic resonance antenna.

FIG. 3 shows a cross-sectional view 300 of a magnetic resonance antenna 100, In this case the cross-section 300 is a semi circle. The first edge 208 and the second edge 210 could be placed on a centric support and the subject could be placed in the semi circle. From within the semi circle, the cross-section 300 is concave 302. A upview is shown in FIG. 4. The line marked 400 shows the location of the cross-section 300 shown in FIG. 3. The first reduced radiation zone 202 and the second reduced radiation zone 206 are also shown. In between the first 202 and the second 206 reduced radiation zone is the irradiation zone 204. There are four copper strip antenna elements 404. Within the first reduced radiation zone 202 there are a number of pre-amplifiers 402 and other electronics. The copper strips 404 are connected to the pre-amplifiers 402. The copper strip antennas 404 are very long and run the entire length of the antenna 100.

To make it easier to detune the elements 404 when the antenna is not in the receive mode there is a number of PIN diodes 406 and/or other electronics located in the second reduced radiation zone 206. These PIN diodes 406 are controlled by electronics in the pre-amplifier 402. There is a flat copper conductors 408 which act as a control for the PIN diodes 406. This enables the very long copper strip antenna elements 404 to be detuned. The flat copper conductors 408 are narrower than the copper strips 404. This means that their impedance at radio frequency are higher. This may enable the control PIN diode 406 without interference from radio frequency signals from a magnetic resonance imaging system.

Figure 5:
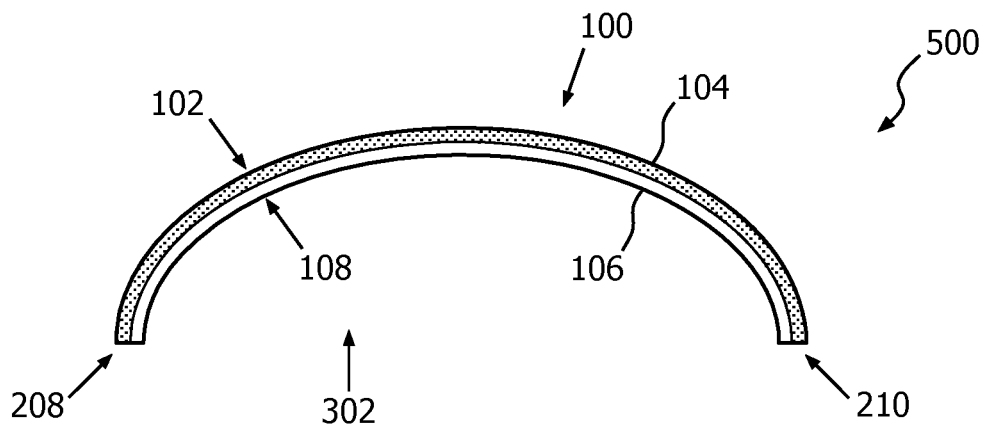
FIG. 5 shows a cross sectional view of a further example of a magnetic resonance antenna.

FIG. 5 shows a cross-sectional view 500 which may be an alternative to that shown in FIG. 3. In this view the cross-sectional view is generally flat and rounded near the ends 208 and 210.

Figure 6:
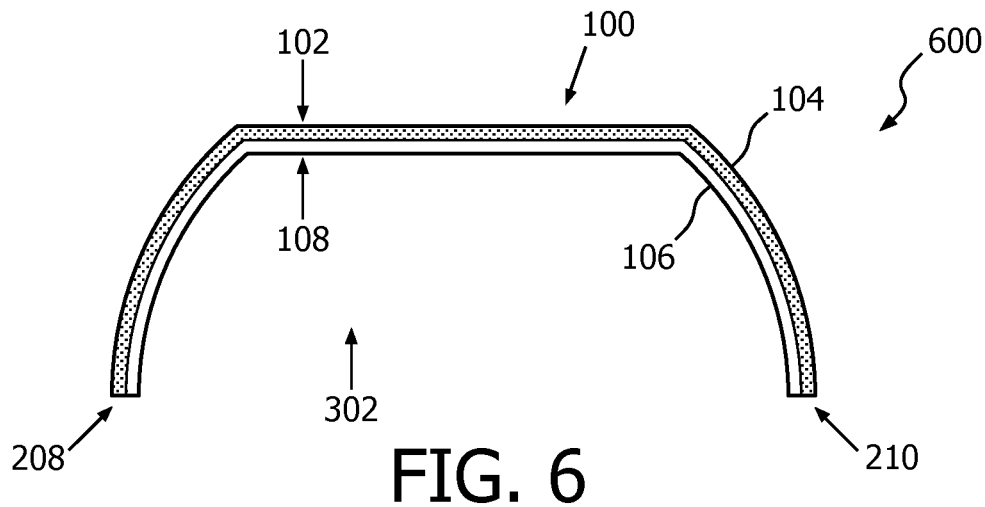
FIG. 6 shows a cross sectional view of a further example of a magnetic resonance antenna.

FIG. 6 shows a further alternative cross-section 600. The cross-section 600 may be used instead of the cross-section 300 shown in FIG. 3. In this cross-section there is a flat portion or straight with rounded edges near the ends 208 and 210. In FIG. 6 there is a mixture of straight segments and curved or rounded segments.

Figure 7:
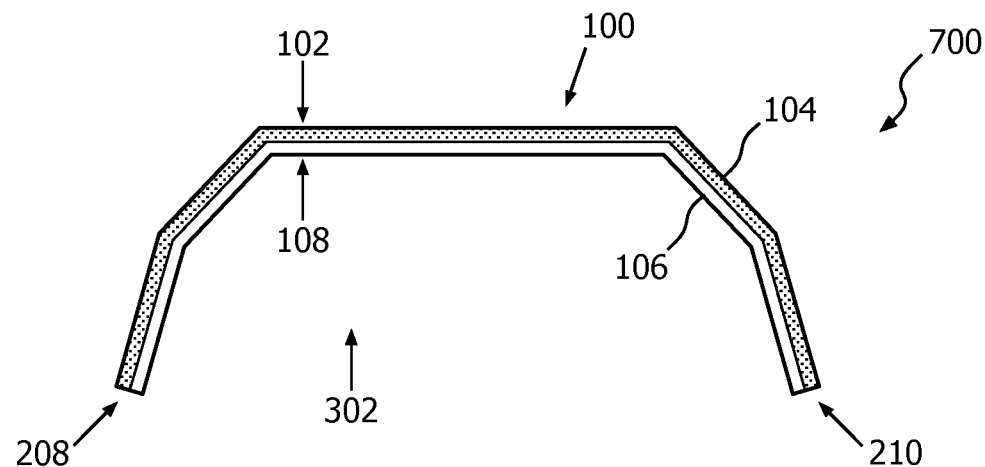
FIG. 7 shows a cross sectional view of a further example of a magnetic resonance antenna.

FIG. 7 shows an alternative cross-sectional view 700 it is an alternative to the cross-sectional view 300 shown in FIG. 3. In this cross-sectional view the cross-section is completely comprised of straight line segments.

It should be noted that in all cross-sectional views shown in FIG. 3, FIG. 5, FIG. 6, and FIG. 7 they are all concave 302 with respect to where the subject would be placed. It may be advantageous to have the antennas be concave in this fashion because as the LINAC rotates the X-ray radiation source about the subject it reduces the amount of antenna that the radiation must pass through. This reduces the amount of attenuation by the antenna 100.

In various example there may be one or there may be several reduced radiation zones. FIGS. 8, 9 and 10 show several different examples. The examples shown in FIGS. 8, 9 and 10 show straight cross-sections. However these straight cross-sections are only exemplary and the coils or antennas may be curved as is illustrated in FIGS. 3, 5, 6 and 7.

In FIG. 8 a cross-sectional view 800 of an antenna 100 is shown. The example is similar to that of the example shown in FIG. 1. There is an electrical connection 802 going to a reduced radiation zone 202. The irradiation zone 204 borders the reduced radiation zone 202. On the other side of the reduced irradiation zone 204 there is a second reduced radiation zone 206.

Another topology is shown in FIG. 9. In FIG. 9 a further cross-sectional view 900 of a magnetic resonance antenna 100 is shown. In this example there is an electrical connection 802 going to a first reduced radiation zone 202. The reduced radiation zone 202 is in contact with the irradiation zone 204.

FIG. 10 shows a further example of the antenna 100 the cross-sectional view 1000 is shown as having two complete sets of coils which border each other. There is an electrical connection 802 going to the first reduced radiation zone 202 and there is a second electrical connection 802 going to the second reduced radiation zone 206. The irradiation zone 204 is divided into two pieces which may have separate antenna elements.

Figure 11:
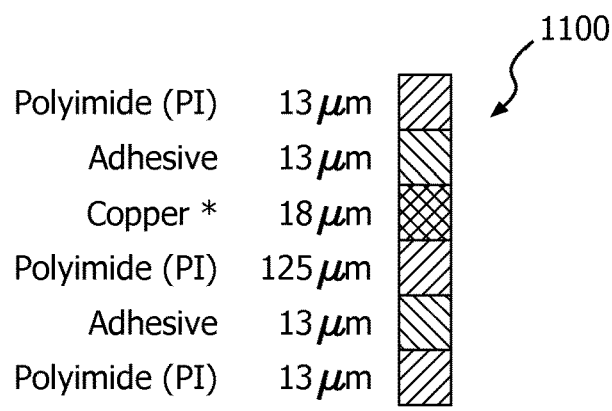
FIG. 11 illustrates a possible stack of materials which may be used to form the structure of a flexible printed circuit board suitable for a magnetic resonance antenna.

Examples of magnetic resonance receive coils may also use Flex printed circuit board (PCB) for the coil elements is made of thin radiation hard PCB substrates and thin and narrow copper traces for electrical connections. An example build-up for the PCB structure is shown in FIG. 11. The PCB is made of thin layers of Polyimide, which has good radiation hardness.

FIG. 11 illustrates the stack of materials which may be used to form the structure 1100 of a flexible printed circuit board suitable for examples. There is a top layer which is formed of polyimide this is connected with an adhesive to a copper layer which is then connected to another polyimide layer another adhesive layer and then a final polyimide layer. The first polyimide layer as shown is being as 13 micrometers thick. This for example may be between five and 25 micrometers. The various adhesive layers may be thicker or thinner. The copper layer is shown as being 18 micrometers. Copper layer thicknesses which work well may for example be between 18 and 35 micrometers thick. The copper is attached to a 125 micrometer polyimide layer. This may be thicker or thinner. For example, this polyimide layer may be between for example 25 to 200 micrometers thick. The lower polyimide layer is shown as being 13 micrometers. This for instance may be between 5 and 25 micrometers thick.

The copper traces that carry RF electromagnetic waves and DC current, are optimized minimally to shadow and attenuate the radiation beam within the irradiation zone. In some examples there may different types of traces or conductors. For example: a) RF trace, purpose of which is to carry RF only; b) DC+RF trace, the purpose of which is to carry both DC and RF, and the DC trace is geometrically located on the left side of the RF trace; and c) RF+DC trace, the purpose of which is the same as in b) with exception that DC trace is right side oriented.

Figure 12:
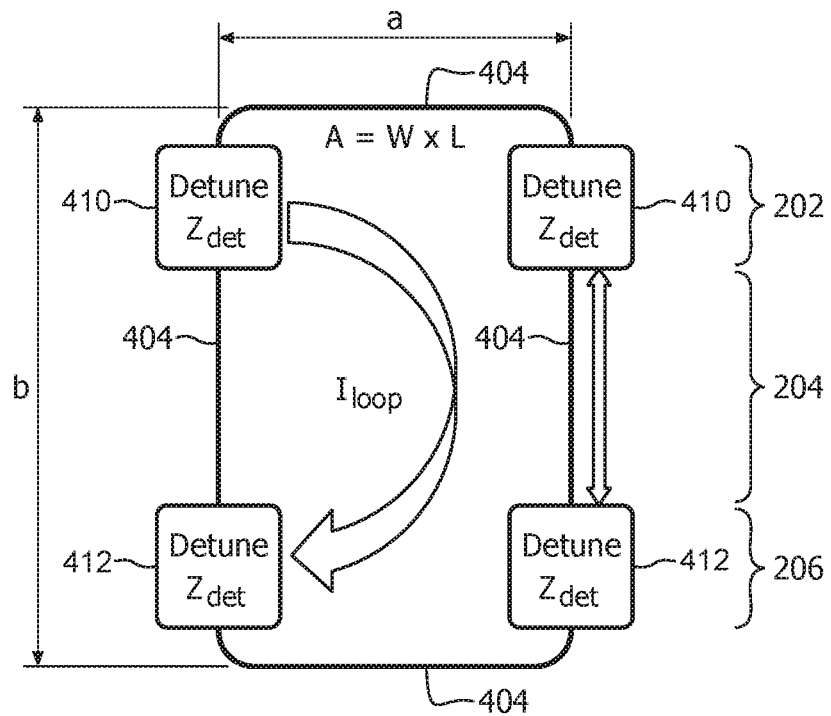
FIG. 12 shows an example of an antenna element with a detune circuits.
Figure 13:
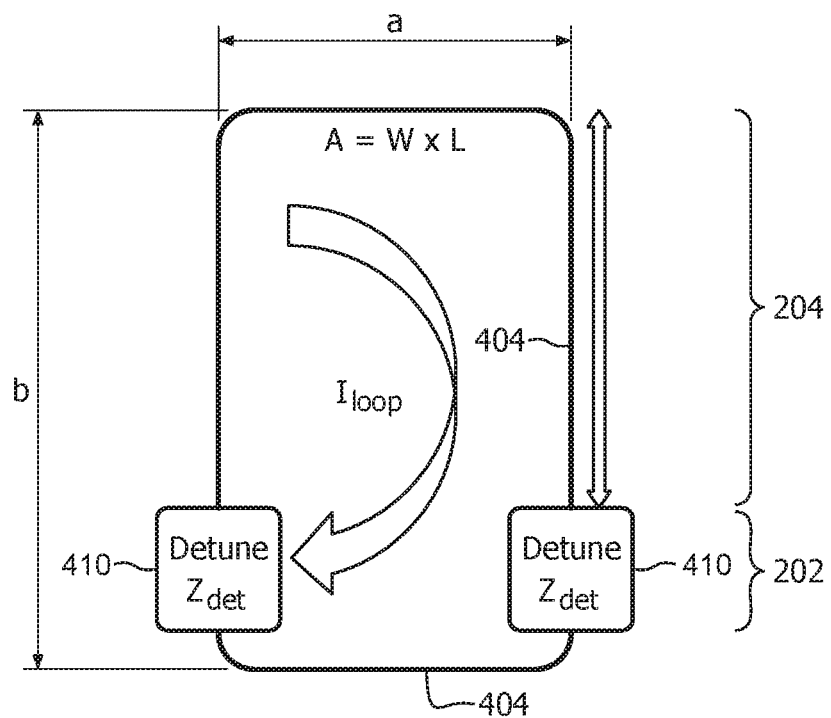
FIG. 13 shows a further example of an antenna element with a detune circuit.

Examples of magnetic resonance receive coils may also have the feature of distributed discrete electronic modules within the coil loop outside the irradiation zone. This optimizes MR performance of the receive coil during the radiation. This may be achieved by distributing multiple detune circuits with high impedance ($Z_{det}$) along the coil loop such way that total impedance during the transmit state of the system is high enough to prevent high transmit power to reduce coil performance. In FIGS. 12 and 13 this is shown the block diagram of two different loops with detune circuits and the irradiation zone.

FIG. 12 shows a detune circuit for an antenna element 404. In the example shown in FIG. 12 the irradiation zone 204 is between the first reduced radiation zone 202 and the second reduced radiation zone 206. Within the first reduced irradiation zone 202 and the second reduced radiation zone 204, there are detune circuits 410,412 that for example may be PIN diodes or other detune circuits.

FIG. 13 shows a further example of an antenna element 404 with its detune circuits 410. In this example there is only one reduced radiation zone 202 which is adjacent to the irradiation zone 204.

High impedance points within the loop, with an area of A, minimize the current flowing in the loop when the loop is exposed to high RF transmit field of B1. The induced voltage u is $$u = -\frac{d[B_1(t) \cdot A]}{dt} \qquad (1)$$
$$= -\omega A B_1 \cos(\omega t)$$

$$\rightarrow |U| = \omega A B_{Lmax}, \text{ where } \omega = 2\pi f. \qquad (2)$$

For a rectangular loop with width of a and length of h, the magnetic field in the center $B_c$ is $$B_c = \frac{2\mu_0 I_{loop} b}{\pi a \sqrt{a^2 + b^2}} + \frac{2\mu_0 I_{loop} a}{\pi b \sqrt{a^2 + b^2}} \qquad (3)$$

Where $I_{loop}$ is the induced current in the loop $$I_{loop} = \frac{|U|}{Z_{det}^{total}} \quad (4)$$

The performance of the coil is not reduced when $B_c \leq 0.1 B_1$ then we can require that:

$$Z_{det}^{total} \geq \frac{20\mu_0 \omega Ab}{\pi a \sqrt{a^2 + b^2}} + \frac{20\mu_0 \omega Aa}{\pi b \sqrt{a^2 + b^2}}, \quad (5)$$

which can be distributed over multiple detune points $Z_{det}^{total} = n_{det} Z_{det}$.

These detune points are distributed such a way that the irradiation zone length is maximized Distributing the coil preamplifiers away from the radiation beam path such a way that the accumulated dose is minimal to enable high image quality over the lifetime. The distance of the preamplifier to the beam iso center x is selected such a way that the dose due to the beam is in the order of 2% or lower at the location of preamplifier, see FIG. 14.

Shielding the coil preamplifiers with materials with high radiation attenuation such way that the dose at the preamplifier is in the order of 2% of the maximum beam dose.

Figure 14:
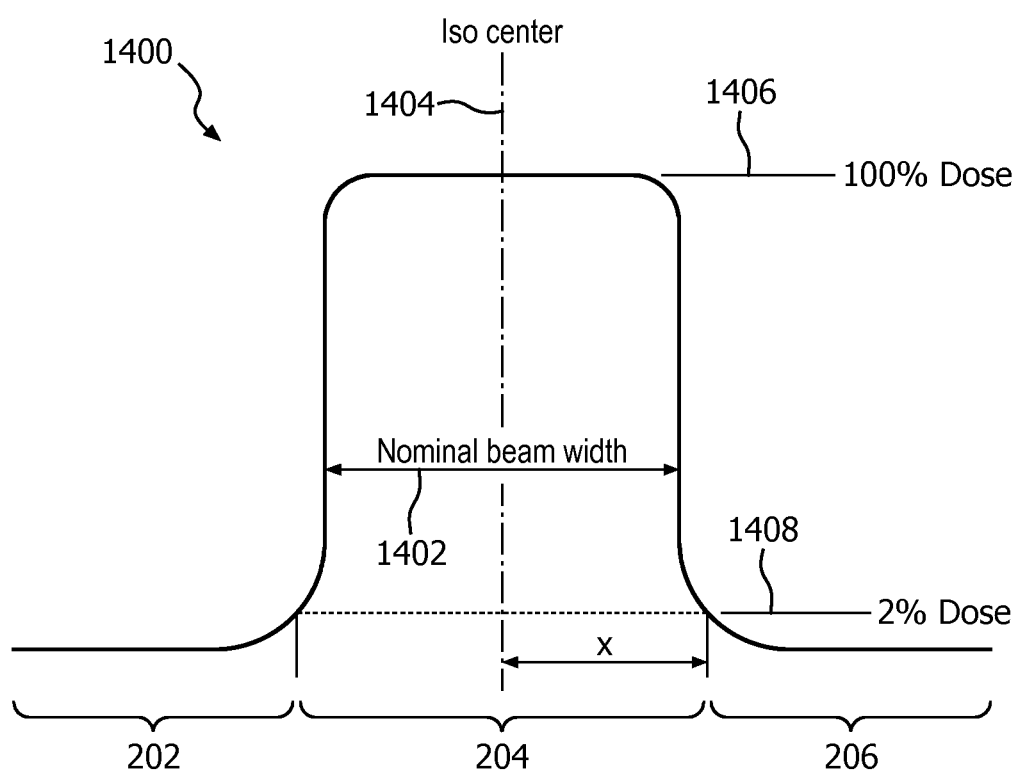
FIG. 14 shows an example of the spatial distribution of radiation from a radiation beam.

FIG. 14 shows an example of the spatial distribution of radiation from a radiation beam 1400, The nominal beam width is labeled 1402, The beam isocenter is labeled 1404. The region of considered to be 100% dose is labeled 1406 and the region labeled 2% dose is labeled 1408. The region above 2% dose is considered to be the irradiation zone 204 and the two regions with 2% and less dose in this example are considered to be the first 202 and second 206 reduced radiation zones.

Figure 15:
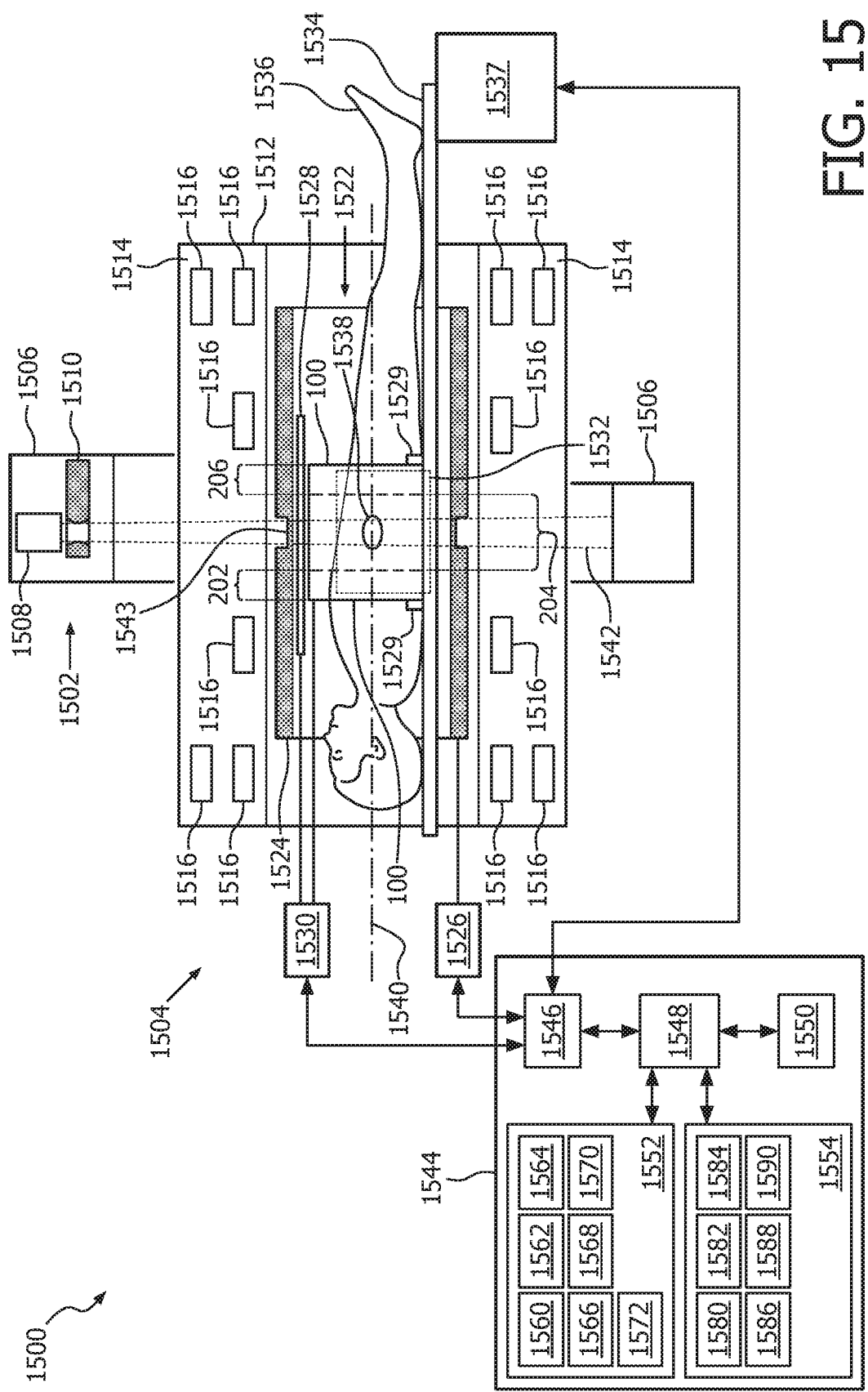
FIG. 15 shows an embodiment of a medical apparatus.

FIG. 15 shows an example of a medical apparatus 1500 according to the invention. The medical apparatus 1500 comprises a LINAC 1502 and a magnetic resonance imaging system 1504. The LINAC 1502 comprises a gantry 1506 and a X-ray source 1508. The gantry 1506 is for rotating the X-ray source 1508 about an axis of gantry rotation 1540. Adjacent to the X-ray source 1508 is an adjustable collimator 1510. The adjustable collimator 1510 may for instance have adjustable plates for adjusting the beam profile of the X-ray source 1508. The adjustable collimator may, for example, be a multi-leaf collimator. The magnetic resonance imaging system 1504 comprises a magnet 1512.

The magnet 1512 shown in FIG. 15 is only an example. It is also possible to use permanent or resistive magnets. The use of different types of magnets is also possible for instance it is also possible to use both a split cylindrical magnet and a so called open magnet.

A split cylindrical magnet is similar to a standard cylindrical magnet, except that the cryostat has been split into two sections to allow access to the iso-plane of the magnet, such magnets may for instance be used to provide a space to for X-ray radiation to reach a subject 1536. An open magnet has two magnet sections, one above the other with a space in-between that is large enough to receive a subject: the arrangement of the two sections area similar to that of a Helmholtz coil. Open magnets are popular, because the subject is less confined, Inside the cryostat of the cylindrical magnet there is a collection of superconducting coils.

The magnet 1512 shown in this example is a modified cylindrical superconducting magnet. The magnet 1512 has a cryostat 1514 with superconducting coils within it 1516. The magnet is designed such that a X-ray radiation beam 1542 does not intersect the superconducting coils 1516. The materials and thicknesses along the beam path 1542 may be chosen to reduce the attenuation of the X-ray radiation. As mentioned above a split or open magnet design may be used instead to eliminate the absorption of radiation by the Magnet 1512.

The magnet 1512 has a bore 1522. Within the bore 1522 of the cylindrical magnet 1512 there is an imaging zone where the magnetic field is strong and uniform enough to perform magnetic resonance imaging.

Within the bore 1522 of the magnet 1512 is a magnetic field gradient coil 1524 for acquisition of magnetic resonance data to spatially encode magnetic spins within an imaging zone of the magnet. The magnetic field gradient coil 1524 is connected to a magnetic field gradient coil power supply 1526. The magnetic field gradient coil 1524 is intended to be representative, to allow radiation to pass through without being attenuated it will normally be a split-coil design. Typically magnetic field gradient coils contain three separate sets of coils for spatially encoding in three orthogonal spatial directions. The magnetic field gradient power supply 1526 supplies current to the magnetic field gradient coils. The current supplied to the magnetic field coils is controlled as a function of time and may be ramped or pulsed.

There is a radio frequency coil 1528 connected to a transceiver 1530. The radio frequency coil 1528 is adjacent to an imaging zone 1532 of the magnet 1512. The imaging zone 1532 has a region of high magnetic field and homogeneity which is sufficient for performing magnetic resonance imaging. The radio frequency coil 1528 may is for manipulating the orientations of magnetic spins within the imaging zone and possibly for receiving radio transmissions from spins also within the imaging zone. The radio frequency coil 1528 may also be referred to as an antenna or channel. The radio frequency coil 1528 may contain multiple coil elements. The radio frequency antenna may also be referred to as a channel.

The radio frequency coil 1528 and radio frequency transceiver 1530 may be replaced by separate transmit and receive coils and a separate transmitter and receiver. It is understood that the radio frequency coil and the radio frequency transceiver are simply representative. The radio frequency antenna is intended to also represent a dedicated transmit antenna and a dedicated receive antenna. Likewise the transceiver may also represent a separate transmitter and receivers.

Also within the bore of the magnet 1522 is a subject support 1534 for supporting a subject 1536. The subject support 1534 may be positioned by a mechanical positioning system 1537. Within the subject 1536 there is a target zone 1538. The axis of gantry rotation 1540 is coaxial in this particular example with the cylindrical axis of the magnet 1512. The subject support 1534 has been positioned such that the target zone 1538 lies on the axis 1540 of gantry rotation. The X-ray source 1508 is shown as generating a radiation beam 1542 which passes through the collimator 1510 and through the target zone 1538. As the radiation source 1508 is rotated about the axis 1540 the target zone 1538 will always be targeted by the radiation beam 1542. The radiation beam 1542 passes through the cryostat 1514 of the magnet. The magnetic field gradient coil 1524 has a gap 1543 which separate the magnetic field gradient coil into two sections. The gap 1543 reduced attenuation of the radiation beam 1542 by the magnetic field gradient coil 1524. Alternatively a split magnetic field gradient coil may be used.

A receive magnetic resonance antenna 100 is placed over the subject 1536. In this example the receive magnetic resonance antenna 100 has two mounts 1529 which attach the antenna 100 to the subject support 1534 in with a controlled geometric relationship. This for example may be used to better estimate the dose received by the subject 1536. It can be seen that the radiation beam 1542 passes through the irradiation zone 204 and for the most pail avoids the first reduced radiation zone 202 and the second reduced radiation zone 206.

The transmit coil 1528 may also be constructed similarly to the coil 100. Discrete components may be moved out side of the path of the beam 1542.

The transceiver 1530, the magnetic field gradient coil power supply 1526 and the mechanical positioning system 1537 are all shown as being connected to a hardware interface 1546 of a computer system 1544. The computer system 1544 is shown as further comprising a processor 1548 for executing machine executable instructions and for controlling the operation and function of the medical apparatus. The hardware interface 1546 enables the processor 1548 to interact with and control the medical apparatus 1500. The processor 1548 is shown as further being connected to a user interface 1550, computer storage 1552, and computer memory 1554.

The computer storage 1552 is shown as containing a treatment plan 1560. The computer storage 1552 is further shown as containing a pulse sequence 1562. A pulse sequence as used herein is a set of commands used to control various components of the magnetic resonance imaging system 1504 to acquire magnetic resonance data 1564. The computer storage 1552 is shown as containing magnetic resonance data 1564 that was acquired using the magnetic resonance imaging system 1504.

The computer storage 1552 is further shown as containing a magnetic resonance image 1566 that was reconstructed from the magnetic resonance data 1564. The computer storage 1552 is further shown as containing an image registration 1568 of the magnetic resonance image 1566. The image registration 1568 registers the location of the image relative to the magnetic resonance imaging system 1504 and the LINAC 1502. The computer storage 1552 is further shown as containing the location 1570 of the target zone 1538, This was identified in the magnetic resonance image 1566. The computer storage 1552 is further shown as containing control signals 1572. The control signals 1572 are control signals which are used to control the LINAC 1502 to irradiate the target zone 1538.

The computer memory is shown as containing a control module 1580. The control module contains computer-executable code which enables the processor 1548 to control the operation and function of the medical apparatus 1500. For instance the control module 1580 may use the pulse sequence 1562 to acquire the magnetic resonance data 1564. The control module 1580 may also use the control signals 1572 to control the LINAC 1502. The computer memory 1554 is further shown as containing a treatment plan modification module 1582. The treatment plan modification module 1582 modifies the treatment plan 1558 using the image registration 1568. The computer memory 1554 is shown as further containing an image reconstruction module 1584. The image reconstruction module 1584 contains code which enables the processor 1548 to reconstruct the magnetic resonance image 1566 from the magnetic resonance data 1564.

The computer memory 1554 is shown as further containing an image registration module 1586. The image registration module 1586 contains code which enables the processor 1548 to generate the image registration 1568 in the location of the target zone 1538 using the magnetic resonance image 1566. The computer memory 1554 is shown as further containing a target zone location module 1588. The target zone location module 1588 contains code which enables the processor 1548 to generate the location of the target zone 1570 using the image registration 1568. The computer memory 1554 is further shown as containing a control signal generation module 1590. The control signal generation module 1590 contains code which enables the processor 1548 to generate the control signals 1572 from the treatment plan 1560 and the location of the target zone 1570, The treatment plan 1560 after it has been modified.

Figure 16:
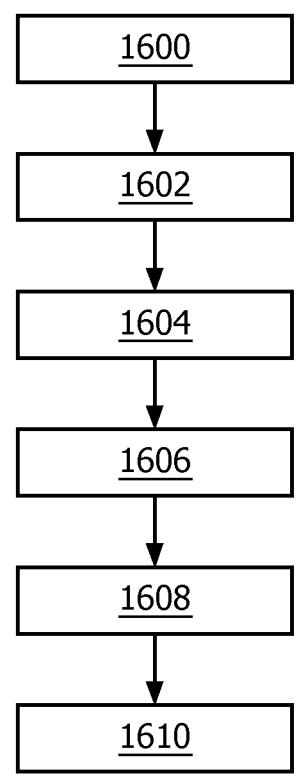
FIG. 16 shows a flowchart which illustrates a method of operating the medical apparatus of FIG. 15.

FIG. 16 shows a flowchart which illustrates a method of operating the medical apparatus 1500 of FIG. 15. In step 1600 a treatment plan 1560 is received. In step 1602 a processor controls the magnetic resonance imaging system 1504 to acquire the magnetic resonance data 1564. Next in step 1604 the processor reconstructs the magnetic resonance image 1566 from the magnetic resonance data 1564. Next in step 1606 the processor registers the location of the target zone 1570 and the magnetic resonance image 1566. This creates an image registration 1568. Next in step 1608 the processor generates the control signals 1572 using the location of the target zone 1570 and the treatment plan 1560. The processor likely also references a model of the apparatus 1560 to generate the correct commands. Finally in step 1610 the processor controls the X-ray radiation source of the LINAC to irradiate the target zone 1538 using the control signals 1572.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS

100 magnetic resonance antenna
102 outer layer
104 flexible printed circuit board
106 coil former
108 biocompatible layer 202 first reduced radiation zone
204 irradiation zone
206 second reduced radiation zone
208 first edge
210 second edge
300 cross sectional view
302 concave surface
400 cross section
402 preamplifier and other electronics
404 copper strips of antenna elements
406 PIN diode and other electronics
408 flat copper conductors
500 cross sectional view
600 cross sectional view
700 cross sectional view
800 cross sectional view
802 electrical connection
900 cross sectional view
1000 cross sectional view
1100 structure of printed circuit board
1400 X-ray radiation beam
1402 nominal beam width
1404 iso center
1406 100% dose
1408 2% dose
1500 medical apparatus
1502 LINAC
1504 magnetic resonance imaging system
1506 gantry
1508 X-ray source
1510 adjustable collimator
1512 magnet
1514 cryostat
1516 superconducting coil
1522 bore
1524 magnetic field gradient coil
1526 magnetic field gradient coil power supply
1528 transmit antenna
1530 transceiver
1532 imaging zone
1534 subject support
1536 subject
1537 mechanical positioning system
1538 target zone
1540 axis of gantry rotation
1542 radiation beam
1543 gap
1544 computer system
1546 hardware interface
1548 processor
1550 user interface
1552 computer storage
1554 computer memory
1560 treatment plan
1562 pulse sequence
1564 magnetic resonance data
1566 magnetic resonance image
1568 image registration
1570 location of target zone
1572 control signals
1580 control module
1582 treatment plan modification module
1584 image reconstruction module
1586 image registration module
1588 target zone location module
1590 control signal generation module
1600 receive a treatment plan for irradiating the target zone
1602 acquire the magnetic resonance data using the magnetic resonance imaging system
1604 reconstruct a magnetic resonance image from the magnetic resonance data
1606 register a location of the target zone in the magnetic resonance image
1608 generate control signals in accordance with the location of the target zone and the treatment plan
1610 control the X-ray radiation source of the LINAC to irradiate the target zone using the control signals

The invention claimed is:

1. A medical instrument, comprising:
a linear accelerator (LINAC) with an X-ray source for directing X-ray radiation at a target zone, wherein the LINAC is adapted for rotating the X-ray source about a rotational axis; and
a magnetic resonance imaging system for acquiring magnetic resonance data from an imaging zone, wherein the target zone is within the imaging zone, the magnetic resonance imaging system comprising a surface receive coil and a magnet for generating a magnetic field within the imaging zone, wherein the X-ray source is adapted for rotating at least partially about the magnet, wherein the surface receive coil comprises:
a plurality of antenna elements;
a plurality of preamplifiers for the antenna elements; and
a rigid coil former for supporting the antenna elements, the rigid coil former having a perimeter and comprising a porous material, wherein: the rigid coil former is divided in tandem into a first reduced X-ray radiation zone, an X-ray radiation zone and a second reduced X-ray radiation zone, wherein no detuning circuitry is located within the X-ray radiation zone; the preamplifiers for the antenna elements are located within the first reduced X-ray radiation zone; the antenna elements are located at least partially within the X-ray radiation zone; the X-ray radiation zone extends continuously from a first edge of the perimeter to a second edge of the perimeter, with the antenna elements adjacent to and not overlapping one another; the antenna elements are disposed between the first edge and the second edge; the first edge and the second edge are opposing edges; and a cross section of the rigid coil former from the first edge to the second edge is substantially concave when observed from a direction from the rigid coil former to the antenna elements.

2. The medical instrument of claim 1, wherein the porous material is any one of the following: a foam, expanded polypropylene, Polyurethane foam, Polyimide foam, polyether ether ketone (PEEK) foam, a corrugated structure, corrugated cardboard, and a honeycomb structure and/or has an attenuation of less than 2 percent for X-ray radiation between 1.8 MeV and 8 MeV.

3. The medical instrument of claim 1, wherein the cross section is any one of the following: a semi-circle; substantially flat with rounded portions near the first edge and the second edge; and a series of connected straight segments.

4. The medical instrument of claim 1, wherein the rigid coil former comprises one or more mounting fixtures for attaching the surface receive coil to a subject support.

5. The medical instrument of claim 1, wherein the antenna elements are disposed on a flexible printed circuit board, wherein the flexible printed circuit board is attached to the rigid coil former.

6. The medical instrument of claim 1, wherein the first reduced X-ray radiation zone and the second reduced X-ray radiation zone each comprise PIN diodes for controlling detuning of the antenna elements, respectively, wherein the X-ray radiation zone comprises conductors for carrying electrical signals between the first and second reduced X-ray radiation zones for controlling switching of the PIN diodes.

7. The medical instrument of claim 1, wherein the surface receive coil further comprises:
   a biocompatible layer that forms a first surface, wherein the rigid coil former is between the first surface and the antenna elements; and
   an outer layer that forms a second surface, wherein the antenna elements are between the second surface and the rigid coil former.

8. The medical instrument of claim 7, wherein the biocompatible layer is any one of the following: Ethylene-vinyl acetate, polyurethane, polyamide foam, polyether ether ketone (PEEK) foam, and polyvinyl chloride (PVC) foam and the outer layer is any one of the following: Ethylene-vinyl acetate, PVC foam, polyurethane, PEEK foam, and PVC foam.

9. The medical instrument of claim 7, wherein the biocompatible layer is laminated to the rigid coil former.

10. The medical instrument of claim 1, wherein a thickness of the porous material is uniform.

11. The medical instrument of claim 10, wherein the medical instrument further comprises:
   a processor for controlling the medical instrument;
   a memory for storing machine executable instructions for execution by the processor, wherein execution of the machine executable instructions causes the processor to:
   receive a treatment plan for irradiating the target zone;
   acquire the magnetic resonance data using the magnetic resonance imaging system;
   reconstruct a magnetic resonance image from the magnetic resonance data;
   register a location of the target zone in the magnetic resonance image;
   generate control signals in accordance with the location of the target zone and the treatment plan; and
   control the LINAC to irradiate the target zone using the control signals.

12. The medical instrument of claim 1, wherein the detuning circuitry comprises a PIN diode.

13. A surface receive coil comprising:
   a plurality of antenna elements;
   a plurality of preamplifiers for the antenna elements; and
   a rigid coil former for supporting the antenna elements and having a perimeter, and comprising a porous material, wherein: the rigid coil former is divided in tandem into a first reduced X-ray radiation zone, an X-ray radiation zone and a second reduced X-ray radiation zone, wherein no detuning circuitry is located within the X-ray radiation zone; the preamplifiers for the antenna elements are located within the first reduced X-ray radiation zone; the antenna elements are located at least partially within the X-ray radiation zone; the X-ray radiation zone extends continuously from a first edge of the perimeter to a second edge of the perimeter with the antenna elements adjacent to and not overlapping one another; the antenna elements are disposed between the first edge and the second edge; the first edge and the second edge are opposing edges; and a cross section of the rigid coil former from the first edge to the second edge is substantially concave when observed from a direction from the rigid coil former to the antenna elements.

14. The surface receive coil of claim 13, further comprising:
   a first surface and a second surface, wherein the rigid coil former is disposed between the first surface and the antenna elements, wherein the antenna elements are between the second surface and the rigid coil former;
   a biocompatible layer that forms the first surface; and
   an outer layer that provides the second surface.

15. The surface receive coil of claim of claim 14, wherein the biocompatible layer is any one of the following: Ethylene-vinyl acetate, polyurethane, polyamide foam, polyether ether ketone (PEEK) foam, and polyvinyl chloride (PVC) foam and the outer layer is any one of the following: Ethylene-vinyl acetate, PVC foam, polyurethane, PEEK foam, and PVC foam.

16. The surface receive coil of claim 14, wherein the biocompatible layer is laminated to the rigid coil.

17. The surface receive coil of claim 13, wherein a thickness of the porous material is uniform.

18. The surface receive coil of claim 13, wherein the X-ray radiation zone has no cutouts.

19. The surface receive coil of claim 13, wherein the detuning circuitry comprises a PIN diode.

20. A surface receive coil comprising:
   a plurality of antenna elements;
   a plurality of preamplifiers for the antenna elements, respectively; and
   a rigid coil former for supporting the antenna elements and having a perimeter, and comprising a porous material, wherein: the rigid coil former comprising an X-ray radiation zone and at least one reduced X-ray radiation zone disposed immediately adjacent to the X-ray radiation zone, wherein no detuning circuitry is located within the X-ray radiation zone; the preamplifiers for the antenna elements are located within the at least one reduced X-ray radiation zone; the antenna elements are located at least partially within the X-ray radiation zone; the X-ray radiation zone extends continuously from a first edge of the perimeter to a second edge of the perimeter, with the antenna elements adjacent to and not overlapping one another; the antenna elements are disposed between the first edge and the second edge; the first edge and the second edge are opposing edges; and a cross section of the rigid coil former from the first edge to the second edge is substantially concave when observed from a direction from the rigid coil former to the antenna elements.

21. The surface receive coil of claim 20, further comprising:
   a first surface and a second surface, wherein the rigid coil former is disposed between the first surface and the antenna elements, wherein the antenna elements are between the second surface and the rigid coil former;
   a biocompatible layer that forms the first surface; and
   an outer layer that provides the second surface.

22. The surface receive coil of claim of claim 21, wherein the biocompatible layer is any one of the following: Ethylene-vinyl acetate, polyurethane, polyamide foam, polyether ether ketone (PEEK) foam, and polyvinyl chloride (PVC) foam and-the outer layer is any one of the following: Ethylene-vinyl acetate, PVC foam, polyurethane, PEEK foam, and PVC foam.

23. The surface receive coil of claim 21, wherein the biocompatible layer is laminated to the rigid coil former.

24. The surface receive coil of claim 20, wherein a thickness of the porous material is uniform.

25. The surface receive coil of claim 20, wherein the X-ray radiation zone has no cutouts.

26. The surface receive coil of claim 20, wherein the detuning circuitry comprises a PIN diode.

* * * * *